(12) United States Patent
Burger et al.

(10) Patent No.: US 8,506,801 B2
(45) Date of Patent: Aug. 13, 2013

(54) DEVICE FOR CAPILLARY CHROMATOGRAPHY AND METHOD FOR MANUFACTURING SUCH A DEVICE

(75) Inventors: Gert-Jan Burger, Hengelo (NL); Anne Freerk De Jager, Enschede (NL); Harm Jan Van Weerden, Enschede (NL)

(73) Assignee: Concept to Volume B.V., Enschede (NL)

( * ) Notice: Subject to any disclaimer, the term of this patent is extended or adjusted under 35 U.S.C. 154(b) by 552 days.

(21) Appl. No.: 12/024,791

(22) Filed: Feb. 1, 2008

(65) Prior Publication Data

US 2008/0185342 A1 Aug. 7, 2008

(30) Foreign Application Priority Data

Feb. 1, 2007 (NL) .................................... 1033317

(51) Int. Cl.
*G01N 30/02* (2006.01)
(52) U.S. Cl.
USPC .............. 210/198.2; 210/656; 96/101; 95/82; 73/23.35; 73/61.52; 422/70; 436/161
(58) Field of Classification Search
USPC .................... 210/198.2, 656; 96/101; 95/82; 73/23.35, 61.52; 422/70; 436/161
See application file for complete search history.

(56) References Cited

U.S. PATENT DOCUMENTS

| | | | | |
|---|---|---|---|---|
| 5,856,616 A | * | 1/1999 | Maswadeh et al. | 73/23.42 |
| 5,979,221 A | | 11/1999 | Walte et al. | |
| 6,440,725 B1 | * | 8/2002 | Pourahmadi et al. | 435/288.5 |
| 6,612,153 B2 | * | 9/2003 | White et al. | 73/23.42 |
| 6,663,697 B1 | | 12/2003 | Kottenstette et al. | |
| 6,664,104 B2 | * | 12/2003 | Pourahmadi et al. | 435/288.6 |
| 6,666,907 B1 | | 12/2003 | Manginell et al. | |
| 7,456,394 B2 | * | 11/2008 | Cameron et al. | 250/288 |
| 2003/0198021 A1 | * | 10/2003 | Freedman | 361/705 |
| 2006/0210441 A1 | * | 9/2006 | Schmidt et al. | 422/89 |
| 2006/0283324 A1 | * | 12/2006 | Roques | 96/101 |

FOREIGN PATENT DOCUMENTS

| | | |
|---|---|---|
| DE | 19707114 A1 | 9/1998 |
| GB | 2 318 528 A | 4/1998 |
| JP | 61265568 A | 11/1986 |
| JP | 7035737 A | 2/1995 |

(Continued)

OTHER PUBLICATIONS

Lehmann, U. et al. "A miniaturized gas chromatograph for autonomous and longtime measurements." Sensor Proceedings I, 1999, pp. 155-158.*

(Continued)

*Primary Examiner* — Katherine Zalasky
(74) *Attorney, Agent, or Firm* — The Webb Law Firm

(57) ABSTRACT

A device for capillary chromatography comprising at least one first receiving space arranged in a circuit board and of a form such that the first receiving space is suitable for at least partially receiving a coiled part of a capillary separation column. Also a method for manufacturing such a device. Using such a device and method the greatest possible advantage can be gained from both miniaturized and integrated gas chromatographs (minimal dead volumes; integration options; small thermal masses and rapid temperature regulation; low cost price; small dimensions, weight and energy consumption; portable and flexible in use) and from the use of a usual capillary separation column (very good separation; high precision and reproducibility). The capillary separation column can herein be heated uniformly, rapidly and accurately.

15 Claims, 5 Drawing Sheets

(56) References Cited

FOREIGN PATENT DOCUMENTS

| | | |
|---|---|---|
| JP | 2006235379 A | 9/2006 |
| WO | 2004065955 A1 | 8/2004 |
| WO | 2006042727 Z1 | 4/2006 |

OTHER PUBLICATIONS

Lehmann, U. et al. "Micro machined analytical gas chromatograph with a plasma polymerised stationary phase" Sensor Proceedings II, 2001, pp. 487-492.*

* cited by examiner

DEVICE FOR CAPILLARY CHROMATOGRAPHY AND METHOD FOR MANUFACTURING SUCH A DEVICE

FIELD OF THE INVENTION

The invention relates to a device for capillary chromatography. The invention also relates to a method for manufacturing a device for capillary chromatography.

BACKGROUND OF THE INVENTION

Chromatography is one of the oldest chemical analysis methods in which a mixture is separated into individual chemical components. It thus becomes simpler to make a qualitative and quantitative determination of the chemical components in a mixture. In gas chromatography the mixture is guided through a separation column by means of an inert carrier gas: the mobile phase. The separation is based on the differential interactions between the different chemical components in the mobile phase and an immobilized stationary phase: a liquid or solid material with which the inner wall of the separation column is covered or which is arranged on an inert carrier material in the separation column. The retention time of a chemical component in the separation column is a function of the measure of interaction with the stationary phase, the type and the quantity of stationary phase, the length and diameter of the separation column, the type of carrier gas, the flow speed and the temperature. The different chemical components will in principle now leave the separation column at different points in time. These points in time can be determined by guiding the outflow from the separation column to a detector. The different chemical components then appear as more or less sharp 'peaks' in the output of the detector: the chromatogram.

Use is generally made in gas chromatography of a capillary separation column: a thin tube with an internal diameter normally varying from about 0.1 to 0.5 mm and a length normally varying from about 1 to 150 meters. Most capillary separation columns are made of fused silica with a protective layer of polyimide on the outside, although metal capillary separation columns are for instance also known. A very good separation with a high precision and reproducibility can be achieved using such capillary separation columns. In respect of its great length, a capillary separation column is generally at least partially coiled for the purpose of use. It must be possible to heat the capillary separation column, wherein it must be possible to regulate the temperature very precisely and preferably very quickly. For this purpose the coiled capillary separation column is generally placed in a heating oven, the temperature of which can be regulated very precisely. The capillary separation column can thus be brought uniformly and very precisely to a determined desired temperature. Varying of the temperature can however take place only relatively slowly because the thermal mass of the heating oven is relatively large.

For several decades there have also been miniaturized gas chromatographs which are manufactured making use of microstructural technology, wherein the separation column is etched in a suitable material, for instance WO 2006/042727 or WO 2004/065955. Dead volumes can be minimized by miniaturization and integration of the etched separation column, injector and detector. The cost price of the whole system can be lower. The dimensions, the weight and the energy consumption of such microsystems are further relatively small, whereby they can be given a portable form and utilized more flexibly on location. The required heating elements can herein be manufactured in integrated manner and the temperature of the etched separation column can be regulated relatively quickly because of the relatively small thermal masses. It has been found in practice however that the separating properties, precision and reproducibility of such etched separation columns still leave much to be desired. It has moreover been found difficult to heat an etched separation column uniformly since undesirable temperature gradients which are difficult to control readily occur.

DE 19707114 describes a system for capillary chromatography wherein a capillary separation column lies against the inner wall of a heating oven and is heated by means of a heating lamp placed in the oven. The advantage is that the capillary separation column can be heated relatively quickly. The system is however not suitable or hardly so, for manufacture by means of microstructural technology and miniaturization. US 2006/0283324 describes a capillary separation column encapsulated and adhered between two thin layers of fibreglass cloth. The whole is preferably attached by means of spacers to a base surface, for instance a printed circuit board, on which the heating is also arranged. Such a construction has the advantages that it is compact, that the capillary separation column can be heated relatively quickly and that use can be made of a usual capillary separation column with its very good separating properties, high precision and reproducibility. Drawbacks are however, among others, the complexity of the whole, the high cost price of manufacture by means of less usual technology and the undesired temperature gradients which occur.

There therefore exists a need for a system for capillary chromatography which has as far as possible both the advantages of miniaturized and integrated gas chromatographs and the advantages of the use of a more usual capillary separation column, wherein the capillary separation column can be heated uniformly, rapidly and accurately. The invention has for its object to fulfil this need.

SUMMARY OF THE INVENTION

The invention provides for this purpose a device for capillary chromatography, comprising at least one first receiving space arranged in a circuit board and of a form such that the first receiving space is suitable for receiving, preferably in substantially close-fitting manner, a coiled part of a capillary separation column. 'Circuit board' is understood here and in the following to mean a PCB (Printed Circuit Board) in all its embodiments: optionally laminated; with one or more metal layers; having as basic material for instance fibre-reinforced epoxy resin, polyimide or a ceramic material; making use of for instance screen printing or photolithography for the purpose of realizing the electrical circuit, and through-hole or surface-mount techniques for arranging and connecting the electrical or electronic components, MCMs Multi-Chip Modules) or Hybrids (Hybrid Integrated Circuits). 'Close-fitting' is understood to mean that the capillary separation column lies at least on a number of sides substantially against, or connects relatively closely to, walls of the first receiving space. The dimensions of the first receiving space can then be minimal so that the device can be compact and the thermal masses involved are small. There can also be a plurality of first receiving spaces and a plurality of capillary separation columns, for instance as in a device with a backflush provision, an analytical separation column and a backflush separation column. The device here preferably also comprises at least one second receiving space arranged in the circuit board and of a form such that the second receiving space is suitable for receiving a non-coiled part, in particular an end part, of the capillary separation column. Non-coiled parts and the outer ends of the capillary separation column can thus also be accommodated and held in place.

The use of a circuit board has significant advantages. Using known technology the necessary electrical or electronic components, for instance for power supply, communication or control, can be arranged on the circuit board, as well as other components, for instance a chip with fluidic functions or heating means for heating the separation column and the chip. Use can advantageously also be made of for instance usual flip-chip technology or the use of gaskets as seals for the purpose of thus realizing fluidic, electrical and mechanical functions and connections. The receiving spaces can be arranged by means of milling. This is a machining technique which is generally available and which is much applied for instance in the manufacture of circuit boards. Cavities and the like can hereby be arranged relatively simply in the circuit board.

The device preferably also comprises at least one chip with a fluidic function arranged on the circuit board. This chip can for instance comprise an injector and a detector. A high integration can thus be realized. The device preferably also comprises first heating means for heating the capillary separation column and second heating means for heating the chip. The capillary separation column and chip can be heated rapidly and uniformly by arranging the heating elements on the circuit board in the close vicinity of the receiving spaces, for instance on both sides of the capillary separation column, or close to the chip. At least one receiving space is here preferably at least partially filled with a thermally conductive material. The temperature of the capillary separation column can for instance thus be regulated more quickly and unwanted temperature gradients can be minimized. The device can also comprise recesses which serve as thermal insulator, for instance in the form of slots or grooves milled into the circuit board. Desired temperature differences, for instance between the capillary separation column and the chip with the injector and detector, can thus be realized and sustained better and more rapidly.

The device is preferably at least partially encapsulated by a casing, for instance by being moulded in a suitable plastic. As well as providing protection, the casing can also serve as additional thermal insulation between the device and the environment. The device is preferably provided with mechanical, fluidic and/or electrical coupling means, by means of which coupling means the whole can be coupled as exchangeable cartridge to an apparatus for chemical analysis. The for instance pretested and calibrated whole of injector(s), capillary separation column(s), detector(s), heating means and optional other components can thus be replaced as cartridge, instead of for instance only the capillary separation column.

SHORT DESCRIPTION OF THE FIGURES

The invention is elucidated hereinbelow on the basis of non-limitative exemplary embodiments of a device and a method according to the invention. Herein:

FIG. 1c is a partial section of the device along the plane A-A indicated in FIG. 1a;

EXEMPLARY EMBODIMENT OF A DEVICE ACCORDING TO THE INVENTION

Figure 1A:
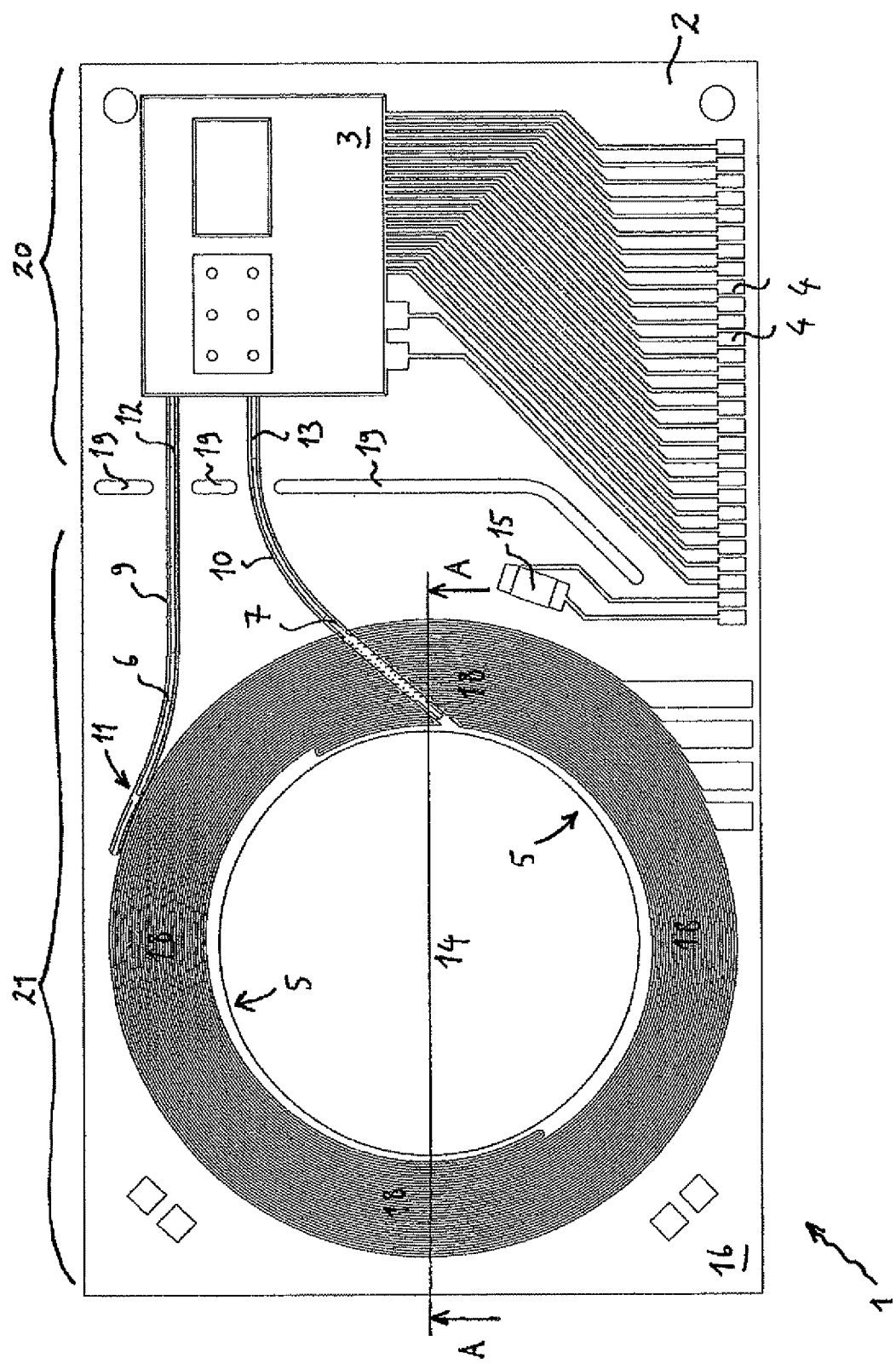
FIG. 1a is a top view of a device according to the invention.
Figure 1B:
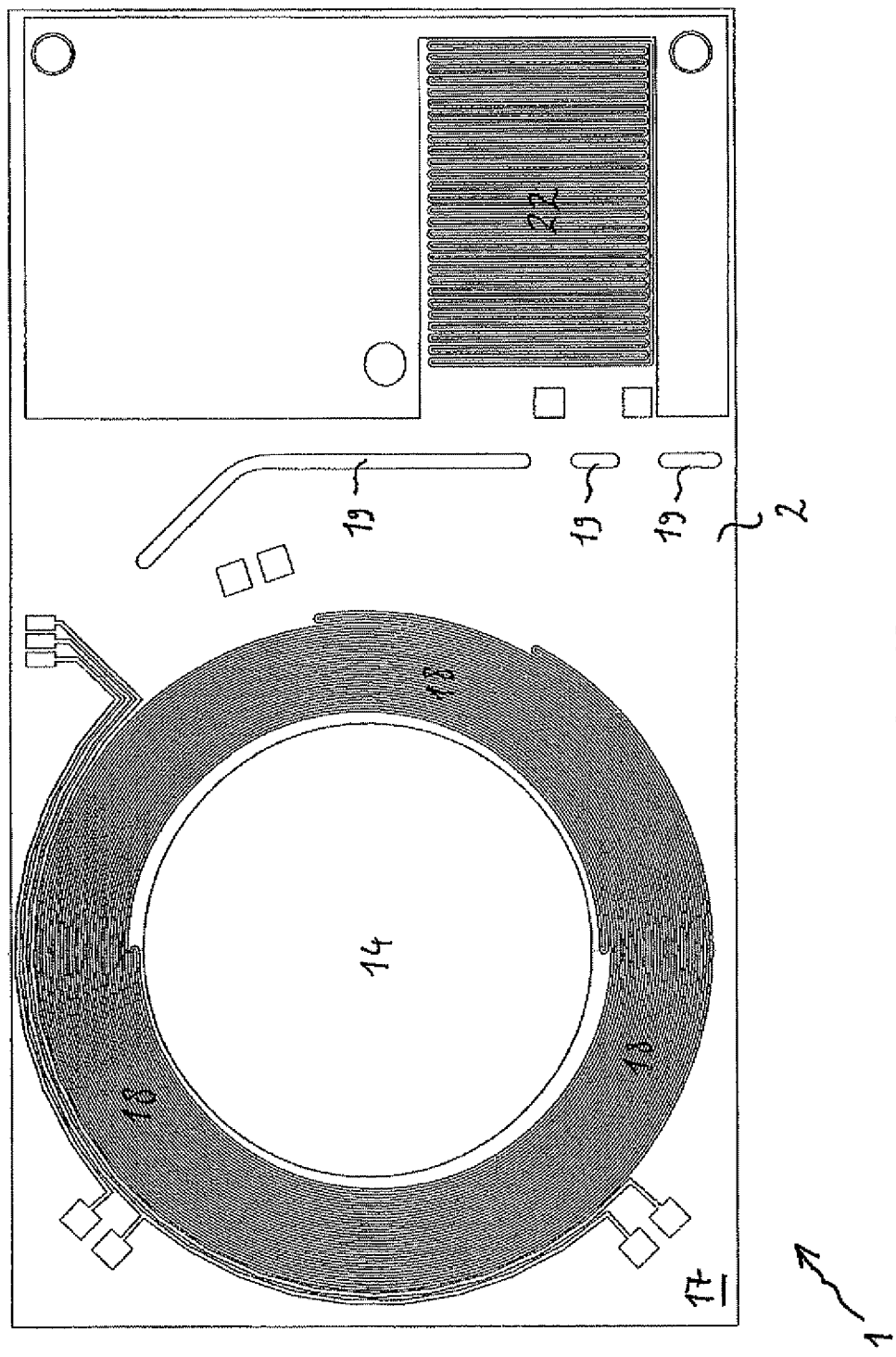
FIG. 1b is a bottom view of the device.
Figure 1C:
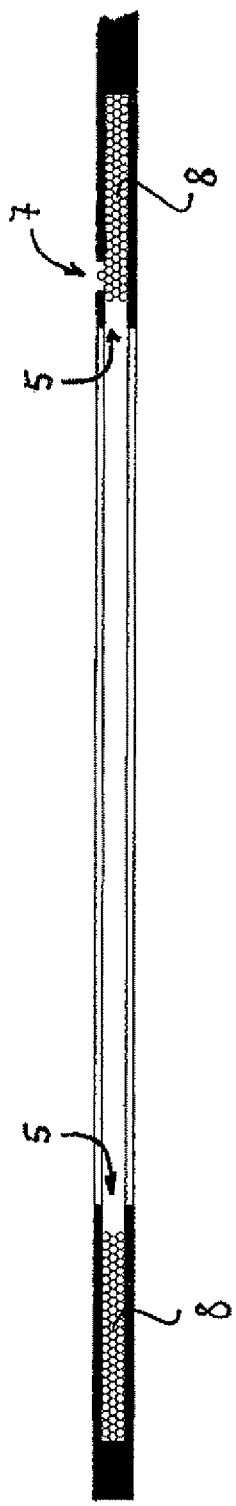
Figure 2:
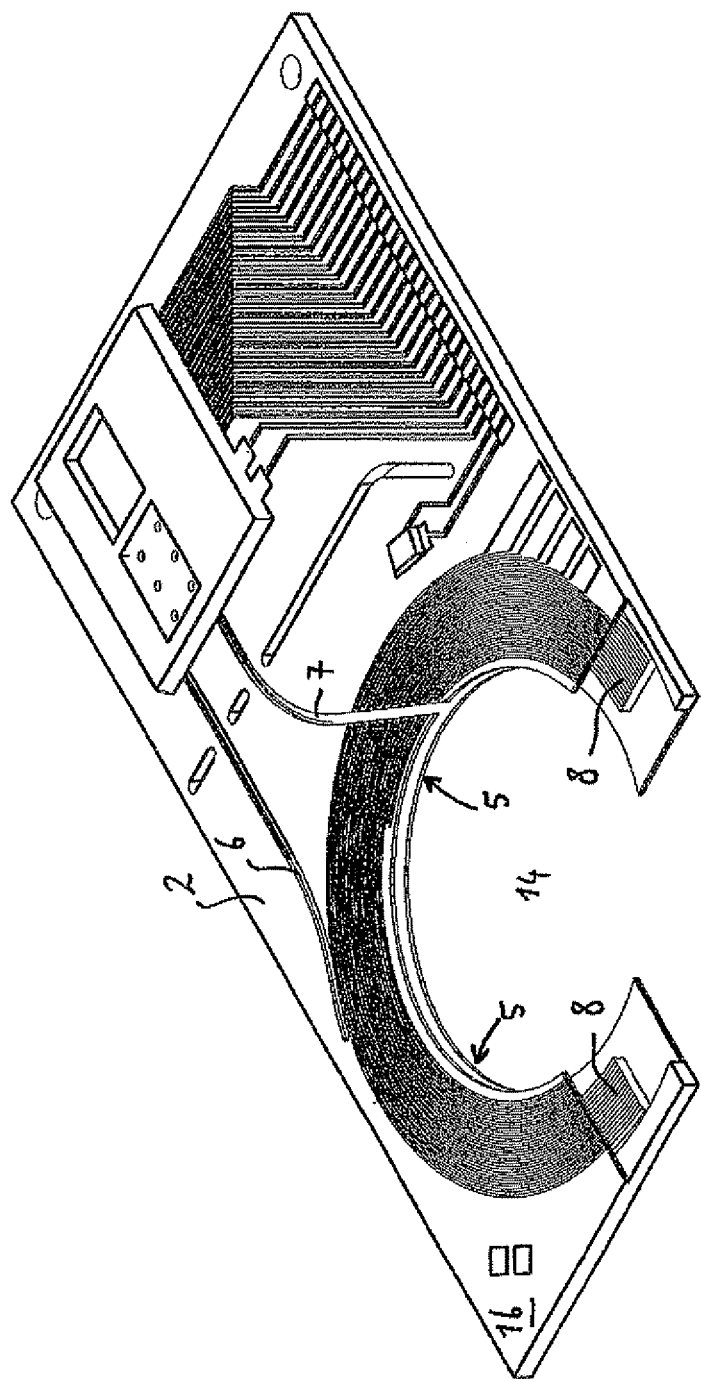
FIG. 2 shows a partially cut-away perspective view of the device.
Figure 3:
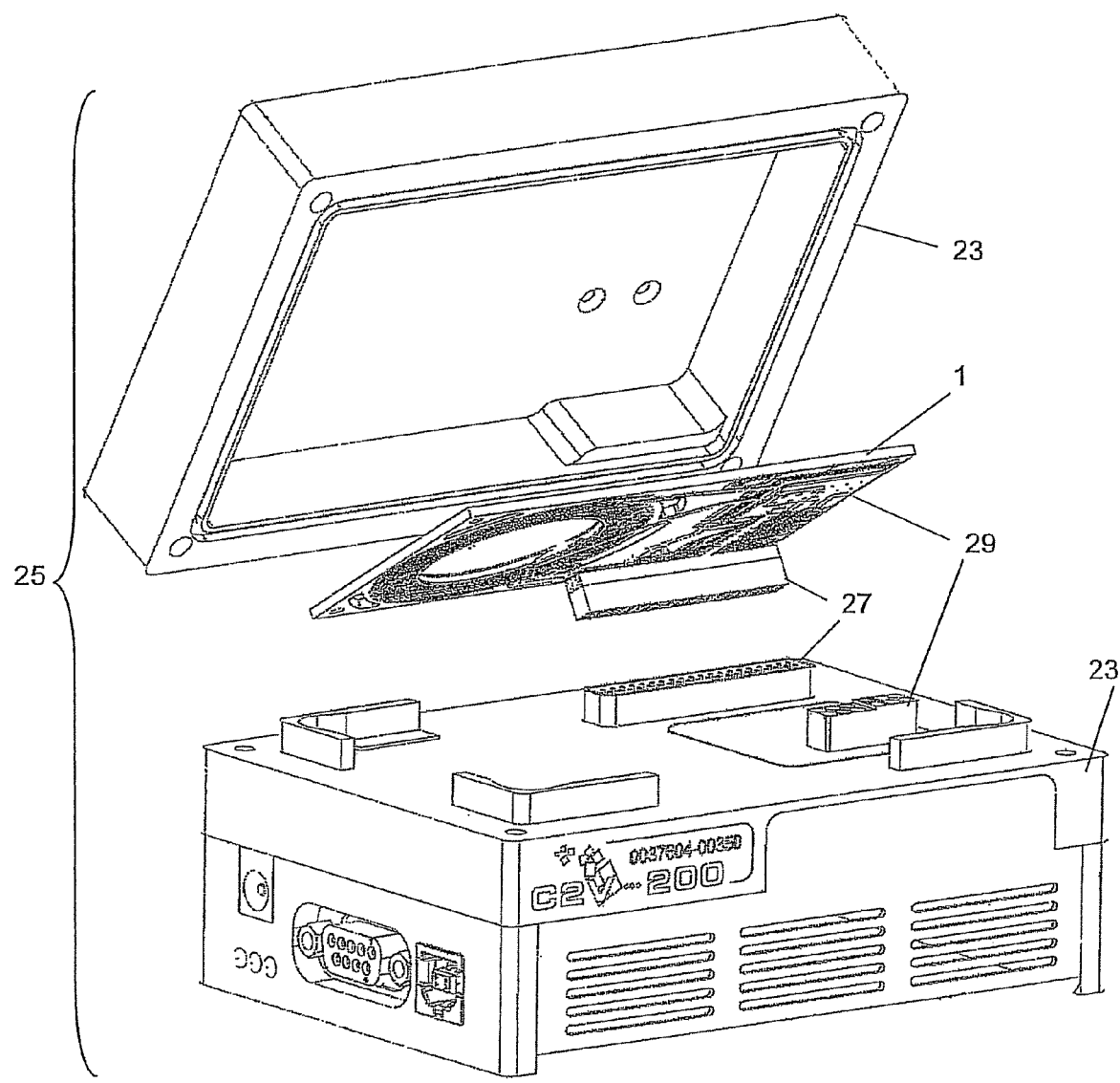
FIG. 3 is an exploded, perspective view of the device accommodated in a housing and a casing.

The device (1) shown in the figures comprises a circuit board (2) on which is arranged a silicon chip (3) comprising an injector, detector and temperature sensor, and provided with electrical connections (4). Milled into the circuit board (2) is a first receiving space (5) in which the coiled part (8) of a capillary separation column is received. Both non-coiled outer ends (9,10) are received in two second receiving spaces (6,7) which are also milled into the circuit board (2) and are open on the top side. In the manufacture of device (1) it is possible to proceed as follows. The first outer end (9) is manoeuvred out of the first receiving space (5) through an opening (11) provided for this purpose and placed from above in the first second receiving space (6) where a connection can be made to for instance a first tube part (12) provided for this purpose. The capillary separation column is then manoeuvred from the centre (14) into the first receiving space (5) and coiled therein. The second outer end (10) is then placed from above in the second receiving space (7) where a connection can be made to for instance a second tube part (13) provided for this purpose.

On the circuit board (2) first heating means (18) are arranged on both the top side (16) and the bottom side (17), in this example conductor tracks for resistive heating of the coiled part (8) of the capillary separation column. The first receiving space (5) can be at least partially filled with a thermally conductive material (not shown) whereby the temperature of the coiled part (8) of the capillary separation column can be regulated even more quickly and undesirable temperature gradients can be minimized still further. The circuit board (2) is also provided with a temperature sensor (15) and a number of slots (19) which are milled into the circuit board (2) and which serve as thermal insulator between part (20) with the silicon chip (3) and part (21) with the coiled part (8) of the capillary separation column. The silicon chip (3) is heated by means of second heating means (22) provided for the purpose.

The device (1) can be encapsulated by a protective casing (25) which can also serve as thermal insulation, for instance by moulding the device in a plastic suitable for this purpose. The device (1) can form a for instance pretested and calibrated exchangeable cartridge. In the given exemplary embodiment the device (1) is placed in a housing (23) provided for this purpose, after which this whole can be built as module into an apparatus for chemical analysis, or a gas chromatograph and coupled thereto by at least one set of mechanical or electrical coupling means (27), fluid coupling means (29) or any combination thereof.

Using such a device and method the greatest possible advantage can now be gained from both miniaturized and integrated gas chromatographs (minimal dead volumes; integration options; small thermal masses and rapid temperature regulation; low cost price; small dimensions, weight and energy consumption; portable and flexible in use) and from the use of a usual capillary separation column (very good separation; high precision and reproducibility). The capillary separation column can herein be heated uniformly, rapidly and accurately.

It will be apparent that the invention is not limited to the given exemplary embodiments, but that diverse variants are possible within the scope of the invention. The first receiving space can for instance also be milled partially into the circuit board and partially into a separate piece of material, after which the separate piece of material is attached to the circuit board so as to thus form a complete first receiving space.

The invention claimed is:

1. A device for capillary chromatography comprising:
at least one receiving space arranged in a circuit board and of a form such that the receiving space is suitable for at least partially receiving a coiled part of a tubular capillary separation column;
wherein the at least one receiving space is an annular receiving space that is defined by an upper wall, a lower wall, and a peripheral wall, and the coiled part of the capillary separation column is at least partially received in the annular receiving space in a substantially close-fitting manner against each said wall of the receiving space;
wherein the annular receiving space surrounds an open center in the circuit board to enable coiling of the capillary separation column into the annular receiving space from the open center; and
wherein heating elements are arranged on both a top side and a bottom side of the circuit board for heating the capillary separation column in a uniform manner.

2. The device as claimed in claim 1, further comprising at least one second receiving space arranged in the circuit board and of a form such that the second receiving space is suitable for at least partially receiving a non-coiled part, in particular an end part, of the capillary separation column.

3. The device as claimed in claim 1, further comprising at least one electronic component arranged on the circuit board.

4. The device as claimed in claim 1, further comprising second heating means for heating at least a part of the chip and arranged on the circuit board.

5. The device as claimed in claim 1, further comprising at least one recess serving as a thermal insulator and arranged in the circuit board.

6. The device as claimed in claim 1, wherein the device is at least partially encapsulated by a casing.

7. The device as claimed in claim 1, further comprising at least one of a set of mechanical, fluidic and electrical coupling means, by means of which coupling means the device can be coupled as an exchangeable cartridge to an apparatus for chemical analysis.

8. A method of manufacturing a device for capillary chromatography comprising the steps of:
arranging at least one annular receiving space that is defined by an upper wall, a lower wall, and a peripheral wall in a circuit board,
the annular receiving space is suitable for at least partially receiving a coiled part of a capillary separation column and surrounds an open center in the circuit board;
providing a non-coiled tubular capillary separation column into the receiving space;
coiling the capillary separation column into the annular receiving space from the open center in a substantially close-fitting manner against each said wall of the receiving space; and
arranging heating elements on both a top side and a bottom side of the circuit board for heating the capillary separation column in a uniform manner.

9. The method as claimed in claim 8, further comprising arranging at least one second receiving space in the circuit board, wherein the second receiving space is given a form such that the second receiving space is suitable for at least partially receiving a non-coiled part, in particular an end part, of the capillary separation column.

10. The method as claimed in claim 8, wherein at least one receiving space is at least partially arranged by means of milling.

11. The method as claimed in claim 8, further comprising arranging at least one electronic component on the circuit board.

12. The method as claimed in claim 8, further comprising arranging on the circuit board a second heating means for heating at least a part of the chip.

13. The method as claimed in claim 8, further comprising arranging in the circuit board at least one recess serving as a thermal insulator.

14. The method as claimed in claim 8, further comprising encapsulating at least a part of the device with a casing.

15. The method as claimed in claim 8, further comprising providing the device with at least one of a set of mechanical, fluidic and electrical coupling means, by means of which coupling means the device can be coupled as an exchangeable cartridge to an apparatus for chemical analysis.

* * * * *

UNITED STATES PATENT AND TRADEMARK OFFICE
CERTIFICATE OF CORRECTION

| | | |
|---|---|---|
| PATENT NO. | : 8,506,801 B2 | Page 1 of 1 |
| APPLICATION NO. | : 12/024791 | |
| DATED | : August 13, 2013 | |
| INVENTOR(S) | : Burger et al. | |

It is certified that error appears in the above-identified patent and that said Letters Patent is hereby corrected as shown below:

In the Claims

Column 5, Lines 16-17, Claim 1, delete "substantially dose-fitting manner" and insert -- substantially close-fitting manner --

Signed and Sealed this
Sixth Day of May, 2014

Michelle K. Lee
*Deputy Director of the United States Patent and Trademark Office*